United States Patent [19]

Alferness

[11] Patent Number: 5,330,496
[45] Date of Patent: Jul. 19, 1994

[54] VASCULAR CATHETER ASSEMBLY FOR TISSUE PENETRATION AND FOR CARDIAC STIMULATION AND METHODS THEREOF

[76] Inventor: Clifton A. Alferness, 2022 235th Pl., Redmond, Wash. 98053

[21] Appl. No.: 695,724

[22] Filed: May 6, 1991

[51] Int. Cl.[5] .............................................. A61B 17/32
[52] U.S. Cl. ................................................... 606/171
[58] Field of Search ............... 606/159, 170, 180, 190, 606/171, 126, 127, 185; 604/158, 164, 170, 264; 128/751–754, 898

[56] References Cited

U.S. PATENT DOCUMENTS

| | | |
|---|---|---|
| 4,166,469 | 9/1979 | Littleford . |
| 4,281,660 | 8/1981 | Fugiwara . |
| 4,309,994 | 1/1982 | Grunwald . |
| 4,401,433 | 8/1983 | Luther . |
| 4,445,509 | 5/1984 | Auth ..................................... 606/159 |
| 4,525,157 | 6/1985 | Vaillancourt . |
| 4,602,645 | 7/1986 | Barrington et al. . |
| 4,624,265 | 11/1986 | Grassi . |
| 4,652,256 | 3/1987 | Vaillancourt . |
| 4,664,120 | 5/1987 | Hess . |
| 4,681,117 | 7/1987 | Brodman et al. . |
| 4,790,825 | 12/1988 | Bernstein et al. . |
| 4,804,359 | 2/1989 | Grunwald et al. . |
| 4,821,735 | 4/1989 | Goor et al. . |
| 4,926,858 | 5/1990 | Gifford, III et al. ................ 606/170 |
| 4,979,939 | 12/1990 | Shiber ................................... 606/170 |
| 4,991,578 | 2/1991 | Cohen ............................... 128/419 D |
| 5,078,723 | 1/1992 | Dance et al. ......................... 606/170 |
| 5,127,917 | 7/1992 | Niederhauser et al. ............. 606/190 |

*Primary Examiner*—Stephen C. Pellegrino
*Assistant Examiner*—William Lewis
*Attorney, Agent, or Firm*—Graybeal Jackson Haley & Johnson

[57] ABSTRACT

A vascular catheter apparatus for penetration through tissue and for cardiac stimulation, and a methods thereof, are disclosed. The apparatus includes a tubular member having a lumen, and a blunt-end stylet within the lumen. An actuation mechanism causes axial movement of the stylet relative to the catheter tube such that the blunt end of the stylet separate tissue for passage of the catheter through the bored tissue. The stylet itself, or an additional stylet, includes a proximal electrode adapted to be oriented in a cardiac chamber and a distal electrode adapted to be oriented adjacent to the epicardium of the heart to cause cardiac stimulation.

20 Claims, 5 Drawing Sheets

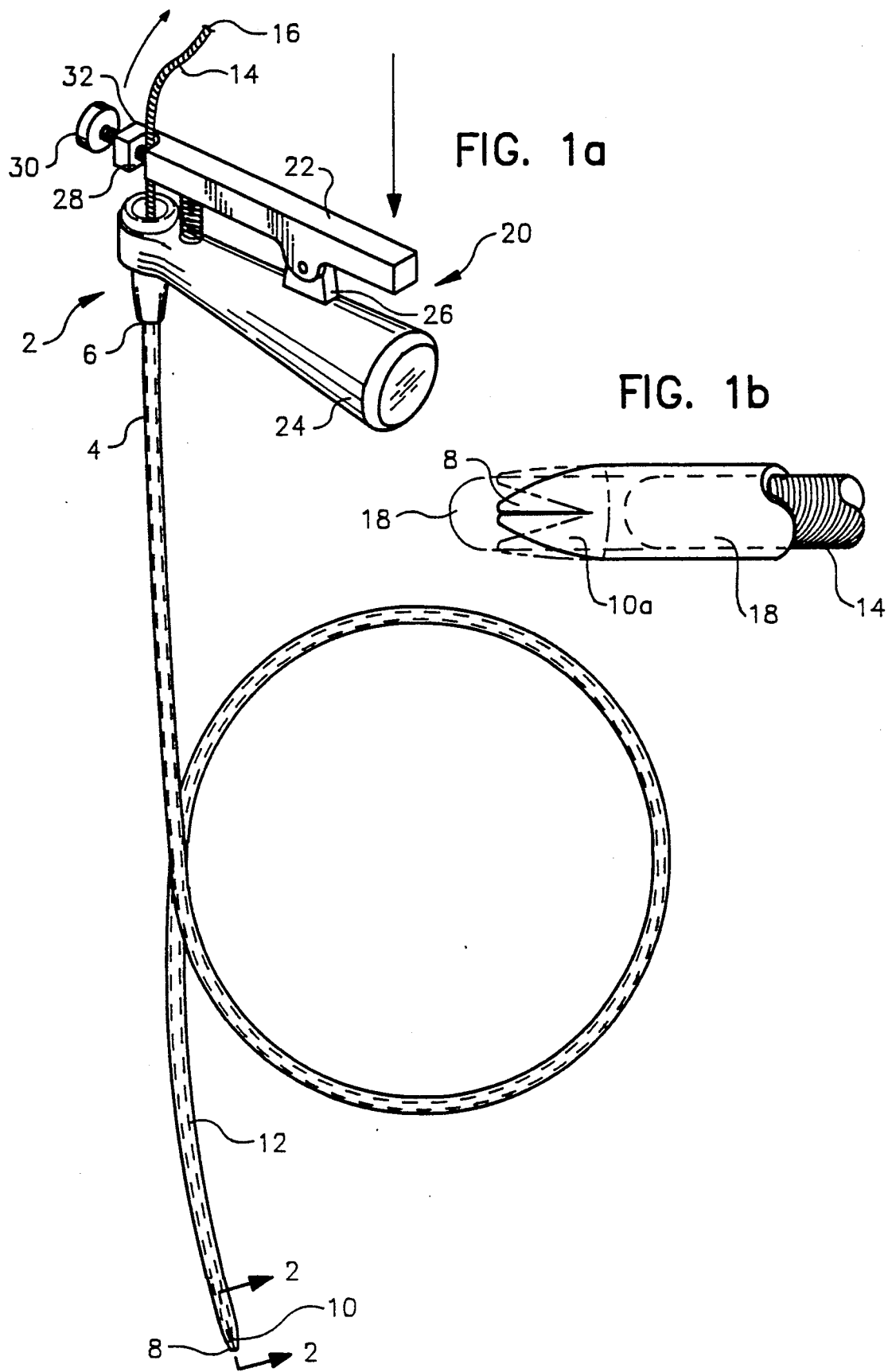

VASCULAR CATHETER ASSEMBLY FOR TISSUE PENETRATION AND FOR CARDIAC STIMULATION AND METHODS THEREOF

BACKGROUND OF THE INVENTION

The present invention pertains to a vascular catheter assembly for penetration through tissue and for cardiac stimulation, and methods thereof. More particularly, the present invention pertains to a tubular member containing a stylet and insertable into a cardiac chamber for blunt boring of an opening through the endocardial, myocardial and epicardial tissue for passage of the tubular member and stylet into the pericardial space. Either the boring stylet itself, or a different stylet can be passed through this opening to provide cardiac stimulation.

The pericardium of the heart includes the pericardial sac, a tough, fibrous membrane surrounding the heart; the pericardial space, a void filled with serous fluid; and the epicardial layer, the exterior surface of the heart. In addition to the pericardium, the heart has the myocardium, a middle, muscular layer; and the endocardium, an inner layer on the walls of the heart's atrial and ventricular chambers.

In order to gain access to the epicardial surface of the heart, for ablation of arrhythmic areas, implantation of defibrillation electrodes or mapping of the epicardial surface, for example, a thoractomy is often required.

In addition to the time, expense, operating and infection risks, and patient discomfort associated with opening the patient's thorax, another problem exists in gaining access to the epicardium by breaching the pericardial sac. Opening the pericardial sac allows the serous fluid to escape and blood to enter the pericardial space inviting additional cardiac complications such as infection and irritation.

A need thus exists for a catheter-based apparatus and method for vascular entry into the body, and particularly into the heart, that circumvents major thoracic surgery and minimizes the amount of organ bleeding that occurs when the stylet passes through organ tissue layers.

SUMMARY OF THE INVENTION

The present invention is a vascular catheter assembly for penetration through tissue (more specifically blunt boring) and for cardiac stimulation, and methods thereof. The vascular catheter assembly includes a tubular member having a lumen, and a blunt-end stylet within the lumen. A stylet activation mechanism causes axial movement of the stylet relative to the catheter tube such that the blunt-end of the stylet separates tissue for passage of the tubular member through the created tissue bore.

In the preferred embodiment of the present invention, the stylet includes a proximal electrode adapted to be oriented in a cardiac chamber and a distal electrode adapted to be oriented adjacent to the epicardium of the heart. However, the present invention also contemplates a stylet distinct from the stylet having the blunt end. This separate stylet is inserted through the created tissue bore after the stylet having the blunt end is withdrawn.

In another aspect of the preferred embodiment, the tubular member has a tapered distal end to initiate the boring and to augment passage of the tubular member and stylet through the tissue bore.

In another aspect of the preferred embodiment, an external tubular sleeve having an internal diameter greater than the external diameter of the tubular member is placed over the tubular member in the tissue bore to enlarge the bore.

In another aspect of the preferred embodiment, an internal tubular sleeve having an external diameter less than the internal diameter of the tubular member, and having an internal diameter greater than the external diameter of the blunt-end stylet is placed over the blunt-end stylet and in the tubular member. The internal tubular sleeve is a skirt placed in the tissue bore to stabilize the bore, and preferably has a biased distal end with teeth that grip the tissue when the internal tubular sleeve is ejected from the tubular member by axial movement of the blunt end stylet.

In another aspect of the preferred embodiment, an optical sensor, either in the blunt end of the stylet or in the distal end of the tubular member, sends signals to an optical receiver denoting stylet position in the heart.

In another aspect of the preferred embodiment, an electrocardiographic sensor on the blunt end of the stylet or in the distal end of the tubular member sends varied signals to an electrocardiographic receiver denoting stylet position in the heart.

In another aspect of the preferred embodiment, the stylet actuation mechanism includes a handle and a spring-biased lever attached to the handle by a fulcrum and connected to the blunt-end stylet. Movement of the spring-biased lever relative to the handle causes axial movement of the blunt-end stylet relative to the tubular member.

In an alternate embodiment, the blunt-end stylet has helical threads for engagement with the tissue.

BRIEF DESCRIPTION OF THE DRAWINGS

These and other features of the present invention will be more fully appreciated when considered in the light of the following specification and drawings in which:

FIG 1a is a perspective view of the vascular catheter apparatus of the present invention;

FIG 1b is an enlarged view of the tapered cylindrical walls of the distal end of the vascular catheter apparatus of the present invention;

FIG. 7b is a distal end view of the embodiment of FIG. 7a.

DETAILED DESCRIPTION OF THE PREFERRED EMBODIMENT

The present invention is a vascular catheter apparatus for penetration of tissue and for cardiac stimulation, and methods thereof.

Figure 1C:
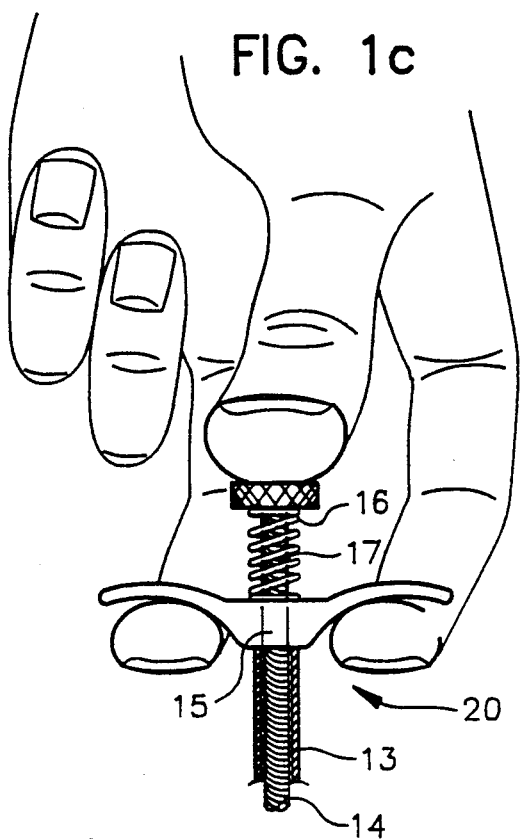
FIG 1c is a perspective view of the vascular catheter apparatus of the present invention having a thumb-activated handle mechanism.
Figure 2:
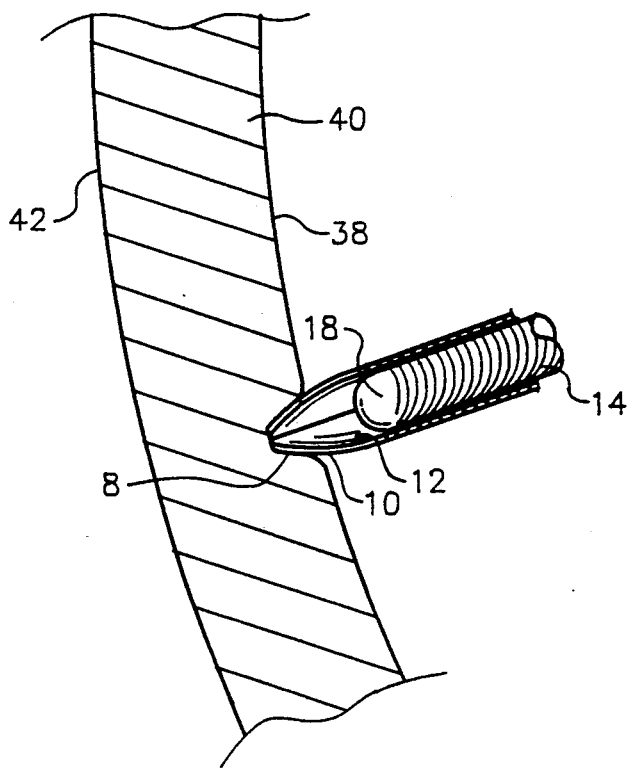
FIG. 2 is a cross-section of the distal end of the vascular catheter apparatus of FIG. 1 taken at lines 2—2.

Referring to FIGS 1a, 1b, and 2, vascular catheter apparatus 2 includes tubular member (or catheter) 4 having proximal end 6 and distal end 8. Distal end 8 preferably has tapered cylindrical walls 10, as shown in FIG. 2, to augment the passage of tubular member 4 through tissue.

Lumen 12 extends axially through tubular member 4 and contains stylet 14, a thin wire capable of maintaining its lengthwise integrity when pushed through an artery or vein. Stylet 14 has proximal end 16 and distal end 18. Stylet 14 is removable from lumen 12 for passage of medical instruments, such as defibrillation electrodes, biopsy probes, or ablation devices, through lumen 12. Referring specifically to FIG. 2, distal end 18 of stylet 14 is a blunt, rounded probe preferably having a cross-sectional area greater than the cross-sectional area of lumen 12 at tapered cylindrical walls 10. Thus, upon axial movement of stylet 14 relative to tubular member 4, blunt, rounded distal end 18 contacts tapered cylindrical walls 10 adjacent catheter distal end 8 and expands catheter distal end 8 to pass through tubular member 4. As shown in FIG 1b, it is thus readily apparent that tubular member 4, and specifically, tapered cylindrical walls 10 of distal end 8, is formed from a thin layer of a semi-elastomeric polymer, such as polyethylene, that allows passage of blunt, rounded distal end 18 of stylet 14, and possesses sufficient resilience to return to its original shape when blunt, rounded distal end 18 is retracted. In a preferred embodiment, as shown in FIG 1b, tapered cylindrical walls 10 are comprised of a plurality of conic sections 10a that open radially by passage of blunt, rounded distal end 18. Conic sections 10a, when preferably comprised of polyethylene or the like, have "living hinges" known in the art that allow the above described radial movement. When blunt, rounded distal end 18 is not biasing conic sections 10a outwardly, conic sections 10a preferably contact each other to form an integral cone.

Attached to proximal end 6 of tubular member 4 is probe actuation mechanism 20, preferably comprised of a spring-biased lever 22 attached to a handle 24 by a fulcrum 26. Lever 22 includes a cavity 28 on the end of lever 22 adjacent to catheter proximal end 6, and through which stylet 14 passes. Screw 30, threadedly engaged in end 32 of lever 22, intersects cavity 28 to grip stylet 14, adjacent proximal end 16, in lever 22. In the spring-biased position of lever 22, blunt, rounded distal end 18 of stylet 14 preferably protrudes slightly from catheter distal end 8, for example, by about 1 mm to about 2 mm. Operating lever 22 against the spring bias preferably retracts blunt, rounded distal end 18 of stylet 14 into tubular member 4.

In an alternate embodiment, shown in FIG 1c, probe actuation mechanism 20 includes elongated tube 13 with an axial bore 15 having a spring-biased, thumb operated shaft 17 therein. The shaft 17 is adapted to grip the proximal end 16 of stylet 14 for axial movement of stylet 14 relative to tubular member 4 when the shaft 17 is plunged into the bore 15 of the probe actuation mechanism 20 by the user's thumb.

Figure 3A:
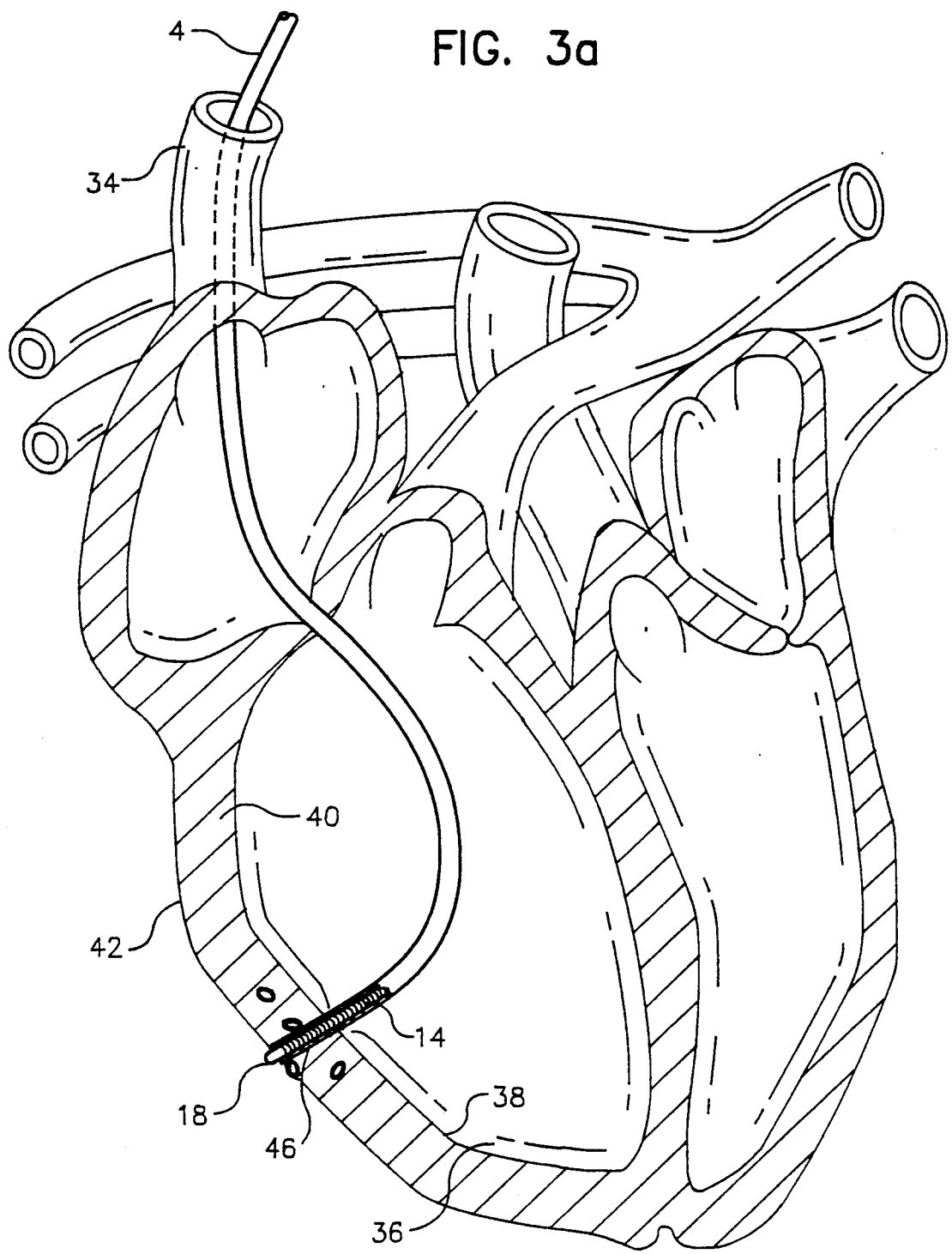
FIG. 3a is a simplified, cross-sectional view of a heart of a patient with a vascular catheter apparatus of the present invention boring through the right ventricle.

Operation of the present invention is now described, with specific reference to blunt boring with an intravenous catheter member from the inner wall of a cardiac chamber to the pericardial space. Referring to FIG. 2 and 3a, tubular member 4 and stylet 14, having blunt, rounded distal end 18, are passed through the vascular system to a vein 34 that leads into the desired heart chamber, for example, the right ventricle 36.

Distal end 8 of tubular member 4 is then pressed against the endocardium 38 of the right ventricle 36 such that tapered cylindrical walls 10 initiate entry of the tubular member 4 into the inner heart tissue and augment passage of tubular member 4 through the tissue as shown in FIG. 2.

Next, probe actuation mechanism 20 is repeatedly operated to cyclically drive the blunt, rounded distal end 18 of stylet 14 against the heart's inner tissue as stylet 14 moves axially relative to tubular member 4. Additionally, tapered cylindrical walls 10, and specifically, conic sections 10a, if present, are biased radially outwardly against the heart's inner tissue as stylet 14 is moved axially relative to tubular member 4. In this manner, blunt, rounded distal end 18 pushes aside the fibrous inner heart tissue and associated cardiac veins as it passes through the endocardium 38, the myocardium 40, and the epicardium 42, as shown in FIG. 3a. Pressure applied by the operator along tubular member 4 causes impact by the blunt, rounded distal end 18 with the heart's inner tissue and urges tubular member 4 and stylet 14 through the tissue bore 46 created by the blunt, rounded distal end 18.

Note that the ball-like tip design of blunt, rounded distal end 18 prevents cutting, slicing, upbraiding, or other severing of major cardiac tissue cellular structure in order to minimize cardiac bleeding. Additionally, once the tubular member 4 and stylet 14 have passed through the tissue bore 46, they may encounter blood vessels that are usually near the exterior heart wall. The blunt shape of distal end 18 pushes aside, rather than severs, these caridac wall vessels.

Each impact of blunt, rounded distal end 18 temporarily damages the heart's inner tissue, electrically stimulating the heart. Thus, in applying the pulsating action to blunt, rounded distal end 18 with probe actuation mechanism 20, the operator should avoid a frequency relative to that of the heart's pulsation that would induce arrhythmias caused by this stimulation. Specifically, impact and catheter advancement should be synchronized to the electrical or mechanical activity of the heart. Proper timing also aids in efficient boring through the heart's inner tissue because the impact of the blunt, rounded distal end 18 with the inner tissue is timed to occur when the tissue tension is low due to the normal heart contraction cycle.

Figure 3B:
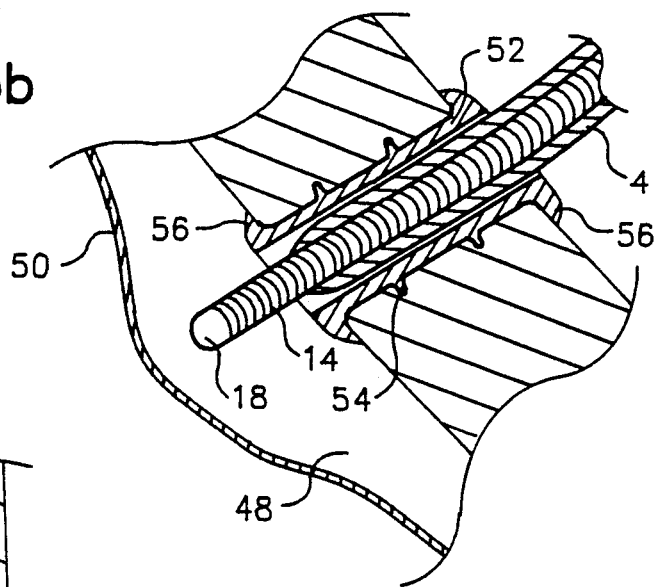
FIG. 3b is a simplified, cross-sectional view of a heart of a patient with a vascular catheter apparatus of the present invention passing through the right-ventricle and into the pericardial space.

Referring now to FIG. 3b, after tubular member 4 and stylet 14 have passed through tissue bore 46 in right ventricle 36, tubular member 4 and stylet 14 enter pericardial space 48. The breakthrough of tissue bore 46 may be somewhat violent and abrupt, resulting in tubular member 4 and stylet 14 passing therethrough with force sufficient to propel stylet 14 against pericardial sac 50. However, the shape of blunt, rounded distal end 18 of stylet 14 prevents piercing of pericardial sac 50 by stylet 14.

Depending upon the size of tubular member 4, the amount of inner tissue damage done by boring, and whether the catheter placement is permanent or temporary, a stabilizing sleeve may need to be inserted into tissue bore 46. FIG. 3b shows a stabilization sleeve in the form of external tubular sleeve 52. External tubular sleeve 52 has an internal diameter greater than the external diameter of tubular member 4 such that external tubular sleeve 52 may be placed over tubular member 4 in coaxial alignment. In this manner, external tubular sleeve 52 can pass through tissue bore 46, enlarging and stabilizing the bore. It is readily apparent that successive external tubular sleeves 52 can be placed over preceding sleeves in order to further enlarge the tissue bore 46. External tubular sleeve 52 can be secured in tissue bore 46 with teeth or threads 54. Further securing external tubular sleeve 52 to tissue bore 46 are lips 56, preformed biased edges of external tubular sleeve 52 that extend radially outward from tissue bore 46.

Figure 4A:
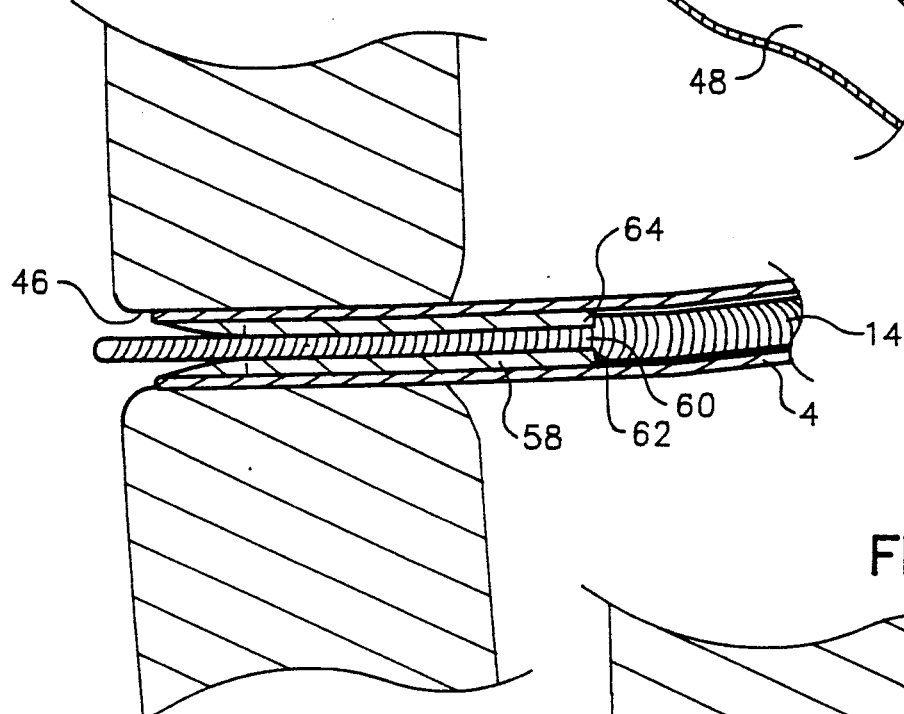
FIG. 4a is a simplified, cross-sectional view of a heart chamber of a patient prior to implantation of a bore stabilizing sleeve by the vascular catheter apparatus of the present invention.
Figure 4B:
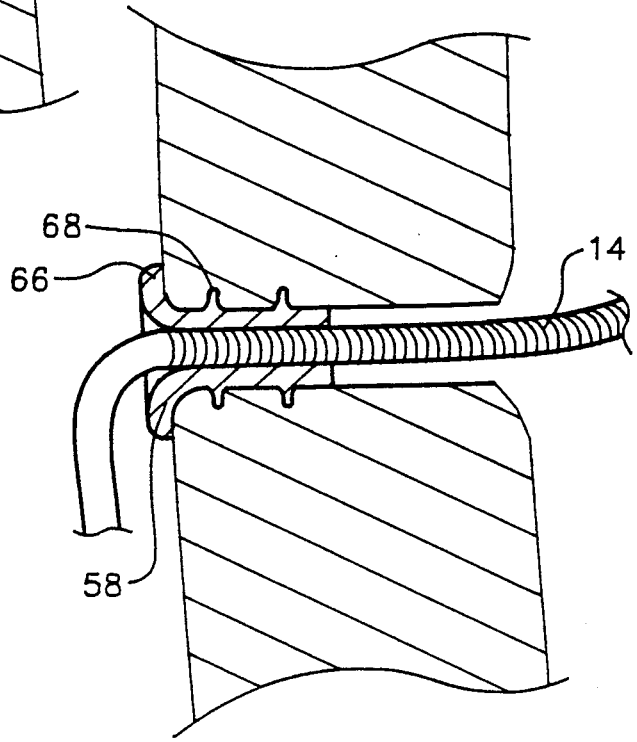
FIG. 4b is a simplified cross-sectional view of a heart chamber of a patient after implantation of a bore stabilizing sleeve by the vascular catheter apparatus of the present invention.

Referring now to FIGS. 4a and 4b, internal tubular sleeve 58 may also be employed to stabilize tissue bore 46. Referring to FIG. 4a, internal tubular sleeve 58 has an external diameter less than the internal diameter of tubular member 4, and has an internal diameter greater than the external diameter of reduced diameter, shouldered distal end 60 of stylet 14. Thus, internal tubular sleeve 58 is loaded into tubular member 4 over reduced diameter, shouldered distal end 60. Upon reinserting of tubular member 4 through tissue bore 44 and implementation of probe actuation mechanism 20, the axial movement of stylet 14 relative to tubular member 4 will urge internal tubular sleeve 58 out of tubular member 4 due to the contact between the shoulders 62 of reduced diameter, shouldered distal end 60 and the proximal ends 64 of the internal tubular sleeve 58.

As shown in FIG. 4b, the distal ends 66 of internal tubular sleeve 58 are preferably biased and have teeth 68 such that, upon ejection from tubular member 4, distal ends 66 are urged radially outward from tissue bore 46 to grip tissue bore 46 with teeth 68.

Figure 5:
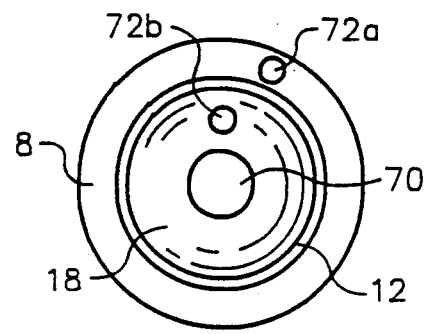
FIG. 5 is a distal end view of the vascular catheter apparatus of the present invention showing optical and ECG sensors.

Referring now to FIG. 5, in the preferred embodiment of the present invention an electrocardiographic sensor 70 is located in the tip of the blunt, rounded distal end 18 of stylet 14 or in the distal end 8 of tubular member 4. Wires passing through tubular member 4 connect ECG sensor 70 to an ECG receiver and an ECG monitor known in the art. The electrically conductive ECG sensor 70 senses electrical ECG signals in the heart tissue. The operator can thus ascertain the relative position of blunt, rounded distal end 18 of stylet 14 in the heart. Specifically, a normal ECG pattern will be sensed by ECG sensor 70 when it contacts the heart's inner tissue. Furthermore, when the blunt, rounded distal end 18 of stylet 14 invades the heart's inner tissue, the ECG signal changes configuration from a normal noninvaded tissue ECG signal to a damaged tissue ECG signal. Once the blunt, rounded distal end 18 passes through tissue bore 44 and into the pericardial space 48, the electrical response signal changes dramatically because ECG sensor 70 is no longer in contact with electrically active cardiac inner tissue.

Still referring to FIG. 5, in the preferred embodiment of the present invention, an optical sensor 72a, such as a fiber optic fiber, is located in the edge of the distal end 8 of catheter 14. Alternatively, the optical sensor, 72b, may be located in the tip of the blunt rounded distal end 18 of stylet 14. A conventional light source and fiber optic receiver known in the art are attached to optical sensor 72a or 72b. The operator can thus ascertain the relative location of blunt, rounded distal end 18 of stylet 14 in the heart. When the blunt, rounded distal end 18 is in the right ventricle 36, the operator views the reddish interior of the ventricle through the optical sensor 72a or 72b. When the blunt, rounded distal end 18 has bored into the inner tissue of the heart, the optical sensor 72a or 72b would transmit a substantially black signal. Once the blunt, rounded distal end 18 has bored through the inner tissue and passed into the pericardial space 48, the optical sensor 72 would transmit a signal showing a white or light environment characteristic of the serous fluid and pericardial sac.

After creation of tissue bore 46 by the impact of blunt, rounded distal end 18 of stylet 14 with the heart's inner tissue, and after insertion of either external tubular sleeve 52 or internal tubular sleeve 58 if required, stylet 14 can be removed and the following surgical devices, and/or procedures, could be employed through tubular member 4: a fiber optic catheter examination of the pericardial space, heart surface and blood vessels; a biopsy probe for heart tissue samples; surgical repairs such as reinforcement of a ventricular aneurism by stitches on the pericardial surface; and ablation of arrhythmogenic tissues.

Additionally, in the most preferred embodiment of the present invention, after creation of tissue bore 46, cardiac stimulation can be implemented with the below described stylet having electrodes. The type of cardiac stimulation that can be induced with the present invention includes defibrillation and conversion of tachycardia. It is important to note that this stylet with electrodes can either be stylet 14 having blunt rounded distal end 18, or alternatively, can be a separate stylet inserted through tissue bore 46 after removal of stylet 14.

Figure 6:
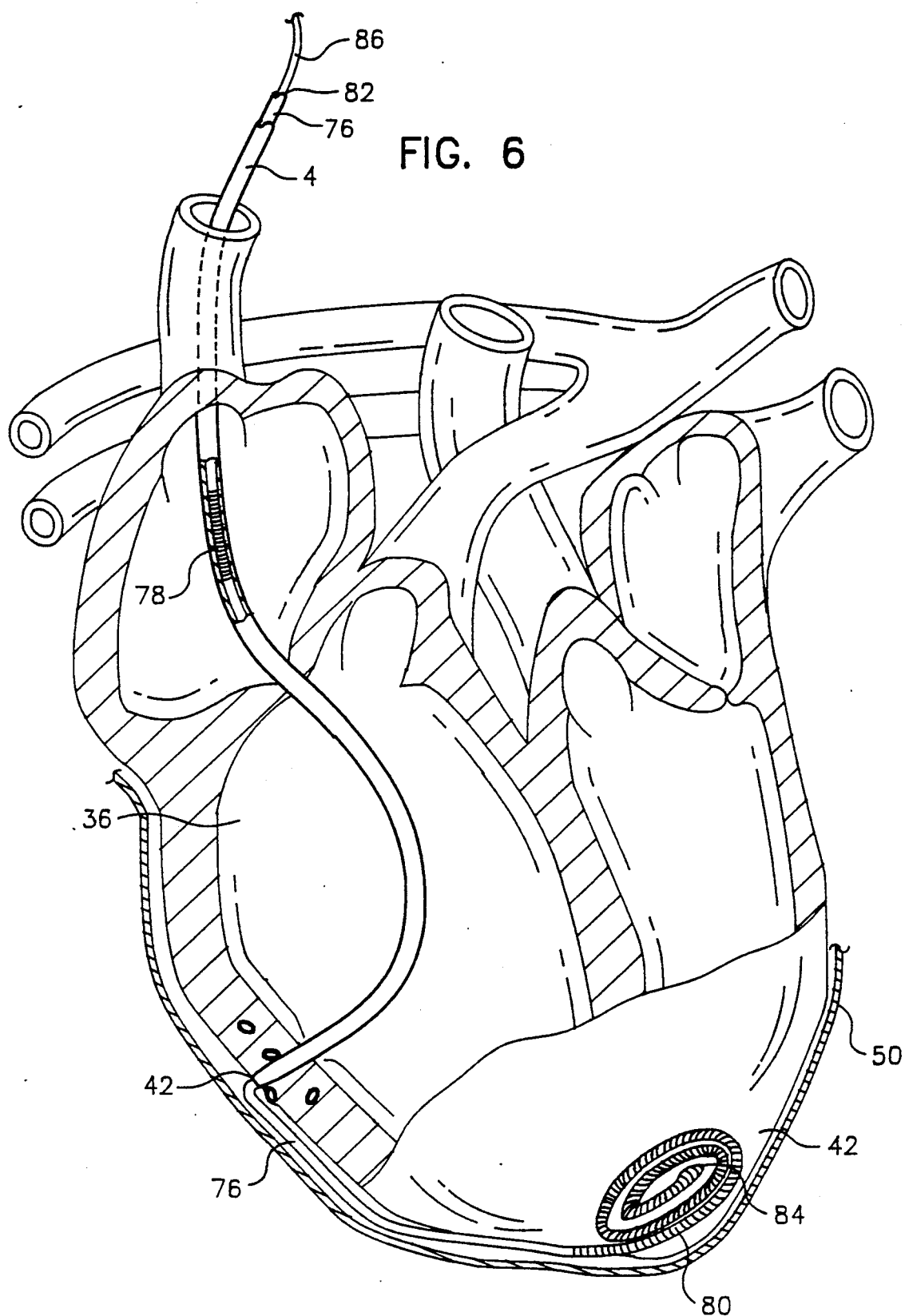
FIG. 6 is a simplified, cross-sectional view of a heart of a patient with the stylet of the present invention including cardiac stimulating electrodes.

Referring specifically to FIG. 6, electrode stylet 76, being either stylet 14 capable of tissue boring or a stylet subsequently inserted through tissue bore 46, includes proximal electrode 78 and distal electrode 80. While electrode stylet 76 is termed a stylet because it is an elongate member inserted through tubular member 4, electrode stylet 76 preferably includes a lumen 82 and has a closed distal end 84 such that a secondary stylet 86 can be inserted through proximal end 88 and into lumen 82 and distal electrode 80 for the reasons described below.

Proximal electrode 78 and distal electrode 80 are comprised of electrical conductive, biologically inert materials known in the art, such as platinum irridium or stainless steel. Either proximal electrode 78 or distal electrode 80 may be the positive pole for cardiac stimulation, with the other of proximal electrode 78 and distal electrode 80 being the negative pole. The energy received by proximal electrode 78 and distal electrode 80 from a power source known in the art (not shown) is preferably between about 10 microjoules and about 40 joules.

Proximal electrode 78 is linearly oriented on electrode stylet 76 such that proximal electrode 78 resides in the right atrium, right ventricle or vena cava. Most preferably, proximal electrode 78 resides in the right atrium or vena cava. Distal electrode 80 is located adjacent to the distal end 84 of electrode stylet 76. Distal electrode 80 is preferably oriented adjacent to the epicardium 42, and can be located at any portion of the epicardium 42 depending upon the desired result of the cardiac stimulation (e.g., defibrillation or conversion of tachycardia). In order to achieve the desired placement of distal electrode 80 on a specific portion of epicardium 42 while ensuring that proximal electrode 78 resides in the desired cardiac chamber, the length of electrode stylet 76 between proximal electrode 78 and distal electrode 80 is varied accordingly.

In order to insert electrode stylet 76 through tissue bore 46, electrode stylet 76 is passed through tubular member 4 until the orientation of proximal electrode 78 in the desired cardiac chamber and the orientation of distal electrode 80 on the desired portion of epicardium 42 is achieved. Specifically, if electrode stylet 76 is required to follow a contour of the heart, as shown in FIG. 6, in order to properly place distal electrode 80, cathode 4 and electrode stylet 76, both being preferably pliable, may be bent accordingly.

Secondary stylet 86 is employed to facillitate passage of distal electrode 80 through tissue bore 46. Distal electrode 80 preferably has a large surface area in order to maximize cardiac stimulation. In its most preferred shape, distal electrode 80 is spiral. Distal electrode 80 is comprised of a resilient material that is biased in this spiral shape. However, when secondary stylet 86 is passed through lumen 82 of electrode stylet 76 and into distal electrode 80, secondary stylet 86 straightens distal electrode 80 for passage through tissue bore 46. After distal electrode 80 is placed at the desired location adjacent to epicardium 42, secondary stylet 86 is withdrawn from distal electrode 80 and lumen 82, and distal electrode 80 returns to its spiral shape.

After proper orientation of proximal electrode 78 and distal electrode 80, electrode stylet 76 can be secured in tissue bore 46 with, for example, external tubular sleeve 52 or internal tubular sleeve 58.

Figure 7A:
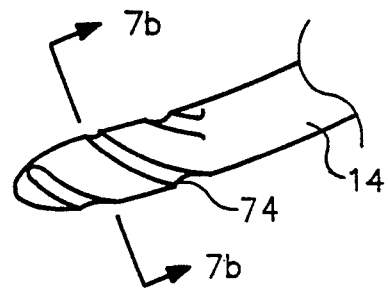
FIG. 7a is a side view of the distal end of another embodiment of the vascular catheter apparatus of the present invention showing helical threads on the stylet end.
Figure 7B:
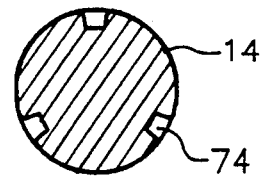

Referring now to FIGS. 7a and 7b, in another embodiment of the present invention, instead of being substantially smooth, the blunt, rounded distal end 18 of stylet 14 has helical threads 74 thereon. Helical threads 74 are preferably fine, shallow threads so that they do not excessively rip or tear cardiac tissue and blood vessels. The helix angle of threads 74 are preferably between about 25 degrees and about 50 degrees. Upon insertion of tapered cylindrical walls 10 into the endocardium 38 of the right ventricle 36 (as previously discussed), the stylet 14 is rotated clockwise or counter-clockwise instead of, or in addition to, its axial movement by probe actuation mechanism 20. The probe actuation mechanism embodiment of FIG. 1c is most conveniently employed to accomplish this rotation. The rotational motion of stylet 14 causes helical threads to bore into the endocardium 38, the myocardium 40, and the epicardium 42, thus creating tissue bore 46 and carrying tubular member 4 and the remainder of stylet 14 therethrough.

While the preferred embodiment pertains to blunt boring of tissue, other types of mechanical tissue penetration, such as, for example, cutting, scraping, probing, piercing and avulsing are contemplated within the scope of the subject invention. Additionally, chemical, electrical and/or thermal penetration means may be employed. While particular embodiments of the present invention have been described in some detail herein above, changes and modifications may be made in the illustrated embodiments without departing from the spirit of the invention.

I claim:

1. A vascular catheter apparatus for blunt boring through inner cardiac tissue and into the pericardial space comprising:

a catheter having a lumen therein, said catheter having a proximal end and a tapered distal end, said catheter insertible through the vascular system to rest in a cardiac chamber adjacent to inner cardiac tissue;

a stylet within said lumen, said stylet having a proximal end and a blunt probe as a distal end; and a probe actuation means including a handle and a spring-biased means on said handle and attached to said proximal end of said stylet wherein movement of said spring-biased means relative to said handle causes axial movement of said stylet relative to said catheter such that said blunt probe separates inner cardiac tissue and for passage through the bored tissue and into the pericardial space.

2. The vascular catheter apparatus of claim 1 further comprising:

an external tubular sleeve having an internal diameter greater than the external diameter of said catheter, said external tubular sleeve adapted to be placed over said catheter and through the bored tissue.

3. The vascular catheter apparatus of claim 1 further comprising:

an internal tubular sleeve having an external diameter less than the internal diameter of said catheter and having an internal diameter greater than the external diameter of said stylet, said internal tubular sleeve adapted to be placed in said catheter and over said stylet for passage through the bored tissue.

4. The vascular catheter apparatus of claim 1 further comprising:

an optical sensing means adjacent said blunt probe of said stylet; and an optical receiving means for receiving signals from said optical sensing means showing the location of said blunt probe in the cardiac chambers, the cardiac tissue and pericardial space.

5. A vascular catheter apparatus for penetrating tissue comprising:

a catheter having a lumen therein;

a penetration means within said lumen, said penetration means having a distal end;

an actuation means for movement of said penetration means relative to said catheter such that said distal end of said penetration means penetrates the tissue for passage through the tissue; and an external tubular sleeve having a internal diameter greater than the external diameter of said catheter, said external tubular sleeve adapted to be placed over said catheter and through the tissue.

6. A vascular catheter apparatus for penetrating tissue comprising:

a catheter having a lumen therein;

a penetration means within said lumen, said penetration means having a distal end;

an actuation means for movement of said penetration means relative to said catheter such that said distal end of said penetration means penetrates the tissue for passage through the tissue; and an internal tubular sleeve having an external diameter less than the internal diameter of said catheter and having an internal diameter greater than the eternal diameter of said penetration means, said internal tubular sleeve adapted to be placed in said catheter and over said penetration means for passage through the tissue.

7. A vascular catheter apparatus for penetrating tissue comprising:
   a catheter having a lumen therein;
   a penetration means within said lumen, said penetration means having a distal end;
   an actuation means for movement of said penetration means relative to said catheter such that said distal end of said penetration means penetrates the tissue for passage through the tissue;
   an optical sensing means adjacent said distal end of said penetration means; and
   an optical receiving means for receiving signals from said optical sensing means.

8. A vascular catheter apparatus for penetrating tissue comprising:
   a catheter having a lumen therein;
   a penetration means within said lumen, said penetration means having a distal end;
   an actuation means for movement of said penetration means relative to said catheter such that said distal end of said penetration means penetrates the tissue for passage through the tissue; said actuation means comprising a handle and a spring-biased means on said handle and attached to said penetration means, wherein movement of said spring-biased means relative to said handle causes axial movement of said penetration means relative to said catheter.

9. A vascular catheter apparatus for blunt boring through cardiac muscle and vascular wall tissue comprising:
   a catheter having a lumen therein and having a proximal end and a distal end, said distal end being tapered;
   a penetration means within said lumen, said penetration means having a blunt distal end with helical threads; and
   an actuation means for repeated axial movement of said penetration means relative to said catheter such that said distal end of said penetration means penetrates the cardiac muscle and vascular wall tissue for passage through the tissue.

10. A vascular catheter apparatus for blunt boring through cardiac muscle and vascular wall tissue comprising:
    a catheter having a lumen therein;
    a penetration means within said lumen, said penetration means having a blunt distal end with helical threads;
    an external tubular sleeve having an internal diameter greater than the external diameter of said catheter, said external tubular sleeve adapted to be placed over said catheter and through the tissue; and
    an actuation means for repeated axial movement of said penetration means relative to said catheter such that said distal end of said penetration means penetrates the cardiac muscle and vascular wall tissue for passage through the tissue.

11. A vascular catheter apparatus for penetrating blunt boring through cardiac muscle and vascular wall tissue comprising:
    a catheter having a lumen therein;
    a penetration means within said lumen, said penetration means having a blunt distal end with helical threads;
    an internal tubular sleeve having an external diameter less than the internal diameter of said catheter and having an internal diameter greater than the external diameter of said penetration means, said internal tubular sleeve adapted to be placed in said catheter and over said penetration means for passage through the tissue; and
    an actuation means for repeated axial movement of said penetration means relative to said catheter such that said distal end of said penetration means penetrates the cardiac muscle and vascular wall tissue for passage through the tissue.

12. The vascular catheter apparatus of claim 11 wherein said internal tubular sleeve is urged into the tissue by axial movement of said penetration means relative to said catheter.

13. The vascular catheter apparatus of claim 12 wherein said internal tubular sleeve has a proximal end and a distal end, said apparatus further comprising:
    a biasing means adjacent said distal end of said internal tubular sleeve, said biasing means urging said distal end radially outward from said catheter tube to contact the tissue when said internal tubular sleeve is in the tissue.

14. The vascular catheter apparatus of claim 13 further comprising:
    teeth adjacent said distal end of said internal tubular sleeve for gripping the tissue when said internal tubular sleeve is in the penetrated tissue.

15. A vascular catheter apparatus for blunt boring through cardiac muscle and vascular wall tissue comprising:
    a catheter having a lumen therein;
    a penetration means within said lumen, said penetration means having a blunt distal end with helical threads;
    an optical sensing means adjacent said distal end of said penetration means;
    an optical receiving means for receiving signals from said optical sensing means; and
    an actuation means for repeated axial movement of said penetration means relative to said catheter such that said distal end of said penetration means penetrates the cardiac muscle and vascular wall tissue for passage through the tissue.

16. The vascular catheter apparatus of claim 15 wherein said optical sensing means is in said distal end of said penetration means.

17. The vascular catheter apparatus of claim 15 wherein said catheter has a proximal end and a distal end and said optical sensing means is in said distal end.

18. A vascular catheter apparatus for blunt boring through cardiac muscle and vascular wall tissue comprising:
    a catheter having a lumen therein;
    a penetration means within said lumen, said penetration means having a blunt distal end with helical threads; and
    an actuation means for repeated axial movement of said penetration means relative to said catheter such that said distal end of said penetration means penetrates the cardiac muscle and vascular wall tissue for passage through the tissue, said actuation means comprising a handle and a spring-biased means on said handle and attached to said penetration means, wherein movement of said spring-biased means relative to said handle causes axial movement of said penetration means relative to said catheter.

19. The vascular catheter apparatus of claim 18 wherein said spring-biased means is a lever attached to said handle by a fulcrum.

20. The vascular catheter apparatus of claim 18 wherein said handle is substantially elongate, said handle having a longitudinal axis with a bore therethrough, and said spring-biased means is a shaft in said bore.

* * * * *